United States Patent
Shiba et al.

(10) Patent No.: US 6,456,885 B1
(45) Date of Patent: Sep. 24, 2002

(54) APPARATUS FOR STRENGTHENING MUSCLES

(75) Inventors: Naoto Shiba; Takashi Maeda; Yoshihiko Tagawa, all of Fukuoka; Toshiyasu Yamamoto, Toyama, all of (JP)

(73) Assignee: Kurume University, Fukuoka (JP)

( * ) Notice: Subject to any disclaimer, the term of this patent is extended or adjusted under 35 U.S.C. 154(b) by 0 days.

(21) Appl. No.: 09/536,695

(22) Filed: Mar. 28, 2000

(30) Foreign Application Priority Data

Mar. 29, 1999 (JP) .............................. 11-087050

(51) Int. Cl.$^7$ ................................ A61N 1/18
(52) U.S. Cl. ....................................... 607/48
(58) Field of Search ................ 482/91, 114, 131; 600/546, 554; 607/48, 49, 77–8, 115

(56) References Cited

U.S. PATENT DOCUMENTS

| | | | |
|---|---|---|---|
| 4,976,264 A | * 12/1990 | Petrofsky | 128/421 |
| 5,116,296 A | * 5/1992 | Watkins et al. | 482/91 |
| 5,976,063 A | * 11/1999 | Joutras et al. | 482/114 |
| 6,064,912 A | * 5/2000 | Kenney | 607/48 |

* cited by examiner

Primary Examiner—Jeffrey R. Jastrzab
Assistant Examiner—Frauces P. Oropeza
(74) Attorney, Agent, or Firm—Jones, Tullar & Cooper, P.C.

(57) ABSTRACT

An improved muscle strengthening apparatus is disclosed which causes "eccentric contraction" of an antagonist muscle of a limb through electrical stimulation so as to apply so-called "closed-kinetic-chain exercises" for the muscles involved to thereby increase the strength thereof. Flexing or extending motion of a knee joint is sensed by a sensor to indicate contraction of the agonist muscle. Upon contraction of the agonist muscle, electrodes placed over the antagonist muscle are energized to cause the eccentric contraction thereof. The invention provides a portable home gymnasium in that it is relatively small, light-weight, cost effective and easy to transport and also relatively simple in construction.

13 Claims, 9 Drawing Sheets

APPARATUS FOR STRENGTHENING MUSCLES

BACKGROUND OF THE INVENTION

The present invention relates generally to an apparatus for exercising muscles of a human being. More particularly, the invention relates to an apparatus for causing "eccentric contraction" of antagonist muscles of a limb through electrical stimulation so as to apply so-called "closed-kinetic-chain exercises" for the muscles to thereby increase the strength thereof. The invention can provide a portable home gymnasium in that it is relatively small, light-weight, cost effective and easy to transport and also relatively simple in construction. In addition, the invention permits a person to receive such closed-kinetic-chain exercises in a comfortable posture and also has the effect of preventing osteoporosis in the bones.

Skeletal muscles are sources of propulsion force needed for various muscular activities and it is important to a proper functioning of the human body to maintain or increase the strength of the muscles. Paralyzed muscles of a limb become debilitated through a process known as "disuse atrophy".

Continued muscle disuse produces deterioration of the tendons and osteoporosis in the bones. Muscle debilitation also occurs when an astronaut is placed in a condition of weightlessness in outer space for a long period of time.

It has been found that debilitated muscles can be restored to near normal functioning, even after years of muscular disuse, through a physical conditioning program based on functional electrical stimulation of the muscles. Typical apparatus for electrically stimulating muscular activity includes pairs of electrodes which may be applied to the surface of the skin above the muscles to be stimulated. Such apparatus generally is designed to passively induce contraction of agonist muscles through electrical stimulation. Due to the passive nature of the electrical stimulation treatment, such systems can conveniently be used for rehabilitation of patients who are in a state of coma or who have experienced a long period of physical inactivity during which muscular deterioration has commenced.

Various types of muscular contraction are known, including (1) mecystactic contraction, (2) isometric contraction, (3) isokinetic contraction, (4) concentric contraction, and (5) eccentric contraction. The mecystactic contraction means a contraction in which muscle tension remains unchanged during contraction. The isometric contraction means a contraction in which muscle tension is increased, but the muscle is not shortened because the resistance cannot be overcome. The isokinetic contraction means a contraction in which the force of a muscle is applied during constant velocity of motion. The concentric contraction means a contraction in which the increase in tension occurs in a muscle as it shortens. Finally, the eccentric contraction means a contraction in which the increase in tension occurs in a muscle as it lengthens.

Also, there are two types of muscular exercises known in the art, including (a) open-kinetic-chain exercise and (b) closed-kinetic-chain exercise. In the open-kinetic-chain exercise, the agonist muscle works or contracts but the antagonist muscle does not work. For example, when a person seated in a chair attempts to extend a knee joint, only the quadriceps muscle which functions as an agonist muscle contracts, while the hamstring muscle functioning as the antagonist muscle does not work or is allowed to extend with the contraction of the agonist muscle. Accordingly, this open-kinetic-chain exercise is effective in strengthening only the agonist muscles.

On the other hand, the closed-kinetic-chain exercise requires both the agonist and antagonist muscles to work or contract simultaneously. For example, during squatting under the action of gravity, the agonist muscle contracts and the antagonist muscle experiences the "eccentric" contraction, i.e., it attempts to contract but is allowed to extend, overcoming the resistance provided by the contraction effort. Accordingly, this closed-kinetic-chain exercise can maintain and increase the strength of both the agonist and antagonist muscles.

Recent studies have revealed that the eccentric contraction is more effective in increasing the strength of muscles than any other types of muscular contraction as described above. It has also been found that the closed-kinetic-chain exercise is more efficient in strengthening muscles than the open-kinetic-chain exercise because co-contraction of the agonist and antagonist muscles results in an increased loading of the agonist muscle.

Accordingly, it is desirable to exercise muscles in an efficient and effective manner by combining the eccentric contraction and the closed-kinetic-chain exercise.

Heretofore, apparatus utilized to exercise muscles of a limb, whether it is of a mechanically loading type or an electrically stimulating type, has used a program based on the open-kinetic-chain exercise. This results in an increased strength of only the agonist muscles, necessitating subsequent and separate application of the same program for the antagonist muscles.

In recent years, various apparatus has been developed which applies the closed-kinetic-chain exercises accompanied by the eccentric contraction for muscles. In such apparatus, a mechanical loading is applied to a muscle to be exercised in a direction tending to cause flexing or extending action of the knee when the knee joint is actively extended or flexed, respectively, in opposition to such loading. Such mechanical loading type devices typically comprise oil cylinders, air cylinders, or springs, etc. and require a user to move his or her limb in a sitting posture as if rowing a boat or to work pedals during stance.

This type of apparatus for increasing the strength of muscles is particularly suited for athletes who desire to enhance their sporting capabilities and also for astronauts who need special training for weightlessness. It is also suitable for use by patients and the aged who have their muscles debilitated, if the loading is appropriately adjusted.

However, such apparatus for applying closed-kinetic-chain exercises for muscles has certain drawbacks as set forth below:

First of all, the apparatus should be equipped with additional and separate means for mechanical loading of the muscles to be exercised, which makes the entire system relatively bulky, complicated in construction and difficult to transport.

Secondly, the apparatus requires a user to assume a special, rather uncomfortable posture during exercise. For example, the user is required to move his or her limb in a sitting stance or during stance. This sometimes makes it impossible for severely injured patients to receive exercises using the apparatus.

SUMMARY OF THE INVENTION

It is, therefore, a principal object of the present invention to overcome the above-said disadvantages of the prior art devices and to provide an improved apparatus for exercising muscles in a manner which applies the closed-kinetic-chain exercise accompanied by the eccentric contraction for the muscles.

It is another object of the present invention to provide an apparatus for strengthening muscles that is relatively small, light-weight, cost effective and easy to transport and also relatively simple in construction.

It is a further object of the present invention to provide such an apparatus for strengthening muscles that does not require a user to assume a specific, rather uncomfortable, posture during exercise.

It is a still further object of the present invention to provide an improved apparatus for exercising muscles in such a manner as to prevent osteoporosis in the bones.

The present invention provides an improved apparatus for strengthening muscles, comprising first means for providing electrical stimulation to an antagonist muscle; second means for sensing a volitionally generated contraction of an agonist muscle; and third means responsive to the second means for actuating the first means to cause eccentric contraction of the antagonist muscle thereby providing resistance to the volitionally generated agonist muscle contraction. The second means provides a contraction signal indicative of contraction of the agonist muscle, and the third means is operative to actuate the first means in response to the contraction signal. The third means comprises fourth means for receiving the contraction signal from the second means and for transmitting an electric signal of muscle stimulating amplitude and waveform to the first means. The first means comprises fifth means for receiving the electric signal of muscle stimulating amplitude and waveform from the fourth means and for transmitting the electric signal to the antagonist muscle to cause eccentric contraction thereof.

The second means comprises an upper portion adapted to be placed on an upper leg portion of a leg; a lower portion adapted to be placed on a lower leg portion of the leg; and an interconnecting portion adapted to join the upper and lower portions for pivotal movement with respect to each other. The second means further comprises a goniometer operatively associated with the interconnecting portion to measure the angle at which the upper portion and lower portion make; and a sensor operatively associated with the goniometer to provide the contraction signal to the third means when the angle measured by the goniometer exceeds a predetermined threshold value.

The second means provides the contraction signal when a user in a sitting posture actively extends his knee. The fourth means is responsive to the contraction signal for transmitting the electric signal to the first means so that electrical stimulation may be provided to a hamstring muscle functioning as the antagonist muscle to cause eccentric contraction thereof. Also, the second means provides the contraction signal when a user lying with his or her face down actively flexes his knee, and the fourth means is responsive to the contraction signal for transmitting the electric signal to the first means so that electrical stimulation may be provided to a quadriceps muscle functioning as the antagonist muscle to cause eccentric contraction thereof.

These and other objects, along with various advantages and benefits of the invention, will be seen in the ensuing description and claims which are accompanied by drawings. The drawings, which are incorporated herein and constitutes part of this specification, disclose a preferred embodiment of the invention according to the best mode contemplated at this time for carrying out the invention.

DESCRIPTION OF THE PREFERRED EMBODIMENT

Figure 1:
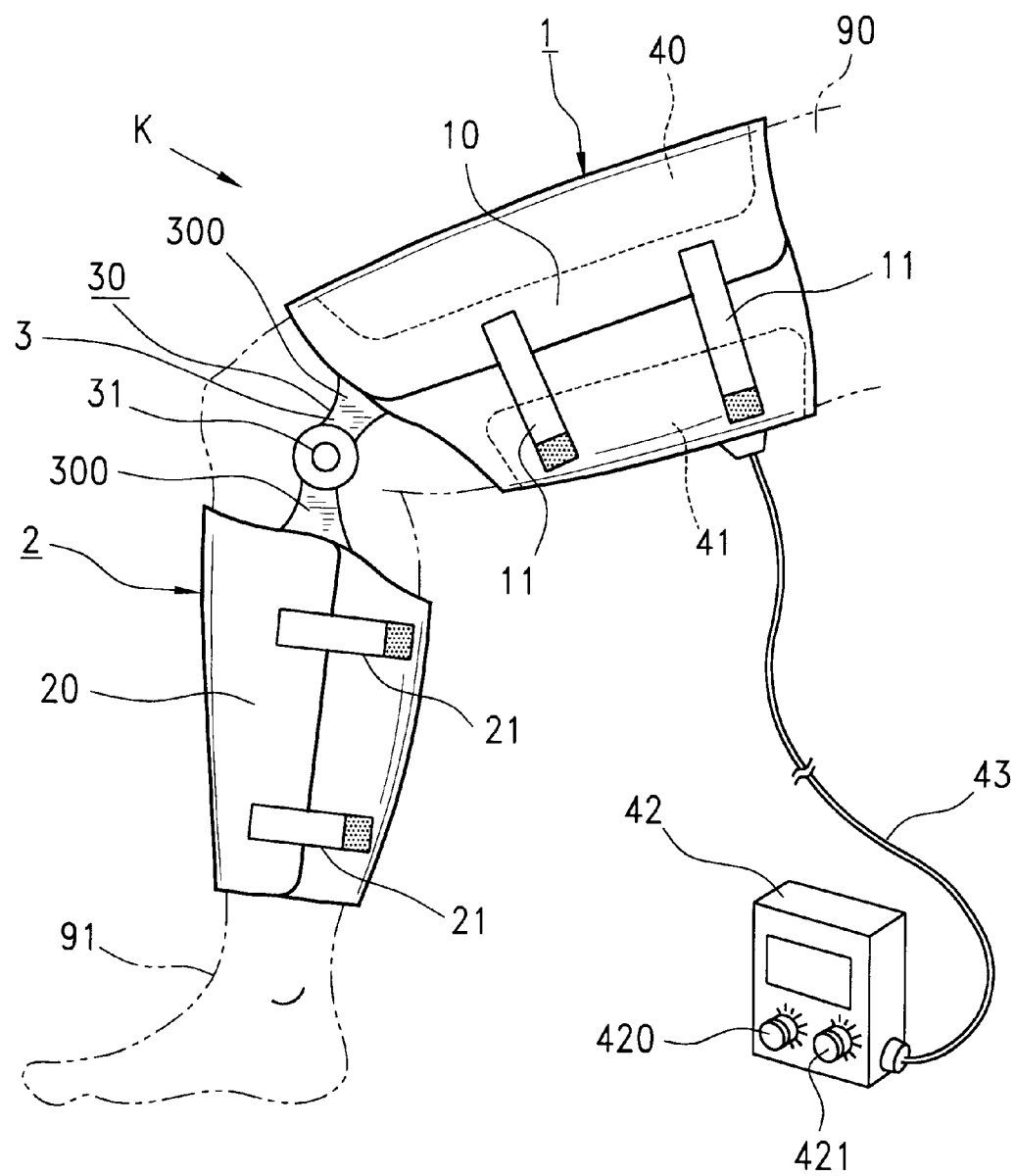
FIG. 1 is a pictorial illustration of the apparatus embodying the invention as attached to the upper and lower leg portions of a user or patient to exercise the quadriceps and hamstring muscles, respectively.

Referring now to the drawings wherein like reference numerals indicate like components or parts of the present apparatus throughout the specification, a muscle strengthening apparatus K embodying the invention is shown in FIG. 1. Although not specifically shown, a user is seated in a chair with his knees in slightly more than 90 degrees of flexion.

The muscle strengthening apparatus, as depicted, comprises an upper portion 1, a lower portion 2 and an interconnecting portion 3 for joining the upper and lower portions 1, 2 together for pivotal movement with respect to each other. In this embodiment, the upper and lower portions 1 and 2 each comprise a compliant or flexible sheet of synthetic material 10, 20 which are adapted for placement over an upper and a lower leg portion of a human body, respectively, in a manner that wraps around the leg portions. Each of the upper and lower portions 1 and 2 includes two fasteners 11, 21 for removably securing them to the upper and lower leg portions. However, it should be noted that the compliant or flexible sheets may be formed of other than synthetic material, such as flexible cloth-like sheets, or somewhat rigid sheets with hinge means. Also, it should be noted that any other fastener means can be used including a hook, a belt, etc.

The upper portion 1 of the muscle strengthening apparatus further includes a pair of compliant or flexible sheet-like electrodes 40, 41 which may be applied to the upper leg portion as illustrated in FIG. 1. These electrodes 40, 41 are applied over a quadriceps muscle and a hamstring muscle, respectively, for the knee joint of the leg. When the user or patient is seated in a chair (not shown), the quadriceps muscle and the hamstring muscle function as the agonist and antagonist muscles, respectively. Other pairs of muscles which function as agonist and antagonist muscles include latissimus dorsi or posterior deltoid and anterior deltoid, and lateral deltoid and pectoralis major for the shoulder joint; triceps and biceps for the elbow joint; extensor carpi radialis longus and brevis and flexor carpi radialis, and extensor carpi ulnaris and flexor carpi ulnaris for the wrist joint; gluteus major or hamstring and quadriceps, and gluteus medius and adducor magnus, brevis or longus for the hip joint; and tibialis anterior and gasrocnemius or soleus for the ankle joint.

The electrodes 40 and 41 are attached to the surface of the skin over the quadriceps and hamstring muscles, as described above. Preferably, they are comprised of a woven sheet of metallic string and a gel-like adhesive layer applied thereon to minimize contact resistance with the skin. Other electrode materials usable for the invention include carbon-rubber electrodes with water-soaked sponges attached thereto. They are placed at locations for providing electrical stimulation to the muscles connected for causing movement of a joint to be loaded. It should be noted that the lower portion of the muscle strengthening apparatus is structurally the same as the upper portion except for the absence of electrodes.

The interconnecting portion 3 includes a goniometer 30 for measuring the angle at which the upper portion 1 and the lower portion 2 of the muscle strengthening apparatus make. The goniometer 30 has a pair of pivotally movable arms 300, 300 which are rigidly attached to the upper and lower portions 1, 2 of the muscle strengthening apparatus.

Operatively associated with the goniometer 30 is a sensor 31 which determines when the angle between the upper and lower portions of the muscle strengthening apparatus exceeds a predetermined threshold value. When the predetermined threshold is exceeded, the sensor 31 provides a signal indicative of contraction or motion of muscles to a controller 42. It should be noted that any other suitable sensors than those with the goniometer 30 may be employed to sense motion of the muscles. Sensors usable include a combination of a hinge and a sensor for sensing the rotational direction thereof, and a sensor for measuring the myoelectric potential generated due to motion of muscles.

The controller 42 is electrically connected to the electrodes 40 and 41 by way of an electric cord 43 to provide an electrical signal of muscle stimulating amplitude and waveform to the electrodes. The controller 42 includes a first control section which is responsive to the sensor output for providing such electrical signal to the electrodes 40, 41 and a second control section which provides the electrical signal of muscle stimulating amplitude and waveform selectively to the particular electrodes irrespective of the sensing by the sensor 31. A change-over switch which can be operated by a knob 420 is operatively associated with both the first and second control sections to selectively actuate them as desired. Depending upon the position of the change-over switch, it is possible to provide the electrical signal of muscle stimulating amplitude and waveform to the electrodes for energization in any one of the following six manners:

(1) The electrode 41 placed over the hamstring muscle functioning as the antagonist muscle is energized when the sensor detects extending action of the knee;

(2) The electrode 40 placed over the quadriceps muscle functioning as the agonist muscle is energized when the sensor detects extending action of the knee;

(3) The electrodes 40 placed over the quadriceps muscle functioning as the antagonist muscle is energized when the sensor detects flexing of the knee;

(4) The electrode 41 placed over the hamstring muscle functioning as the agonist muscle is energized when the sensor detects flexing of the knee;

(5) The electrode 40 placed on the quadriceps muscle is energized by the controller 42 irrespective of the operation of the sensor; and (6) The electrode 41 placed on the hamstring muscle is energized by the controller 42 irrespective of the operation of the sensor.

The controller 42 further includes another knob 421 which enables the user to adjust or modify the electrical stimulation provided by the electrodes 40, 41 by rotating it. A conventional controller may be used as the controller 42 so a detailed explanation of the structure and operation of the controller will be omitted for brevity of explanation.

Figure 2:
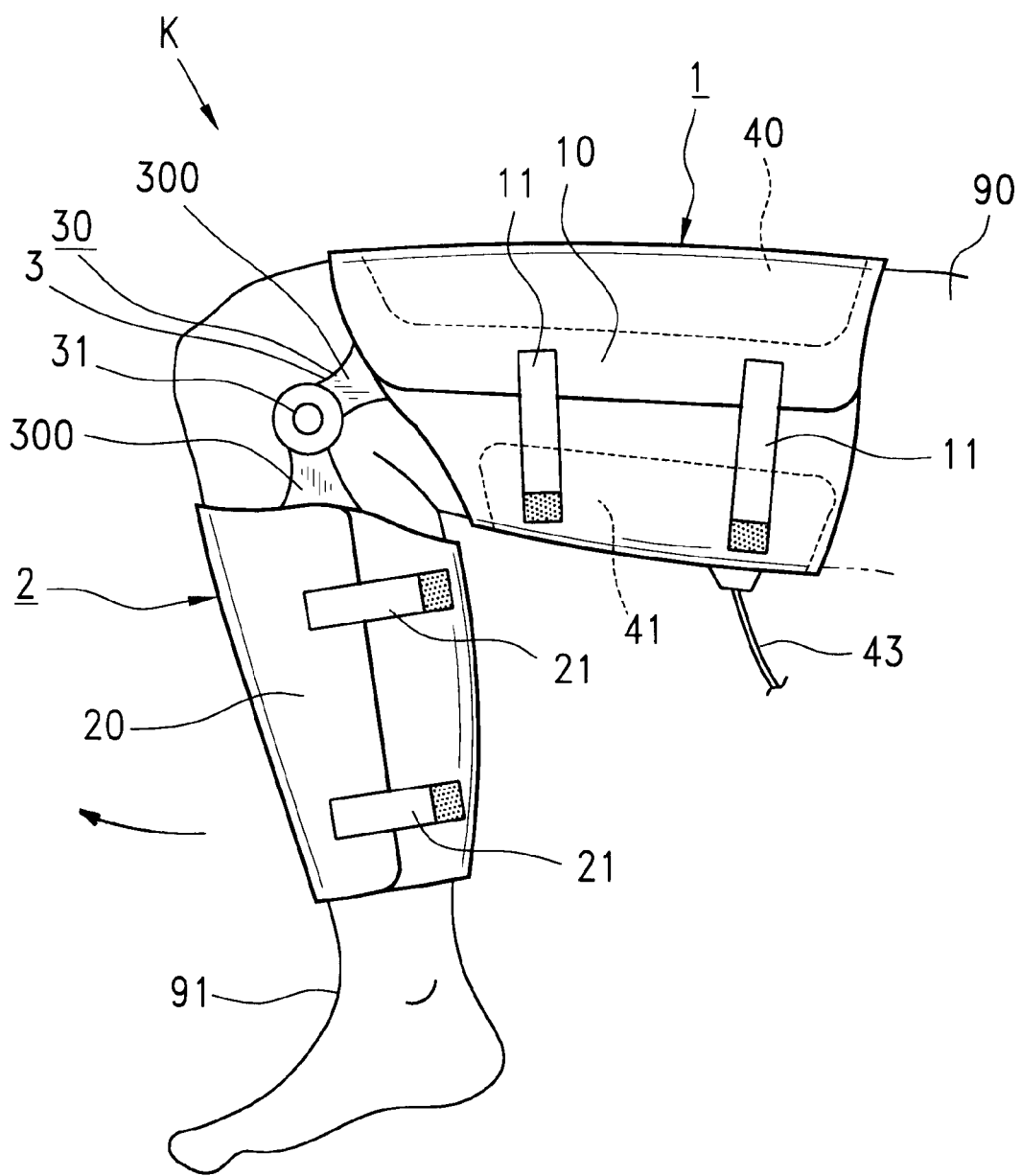
FIG. 2 is a view similar to FIG. 1 showing the present apparatus and the leg prior to the time when the knee joint is actively extended.
Figure 3:
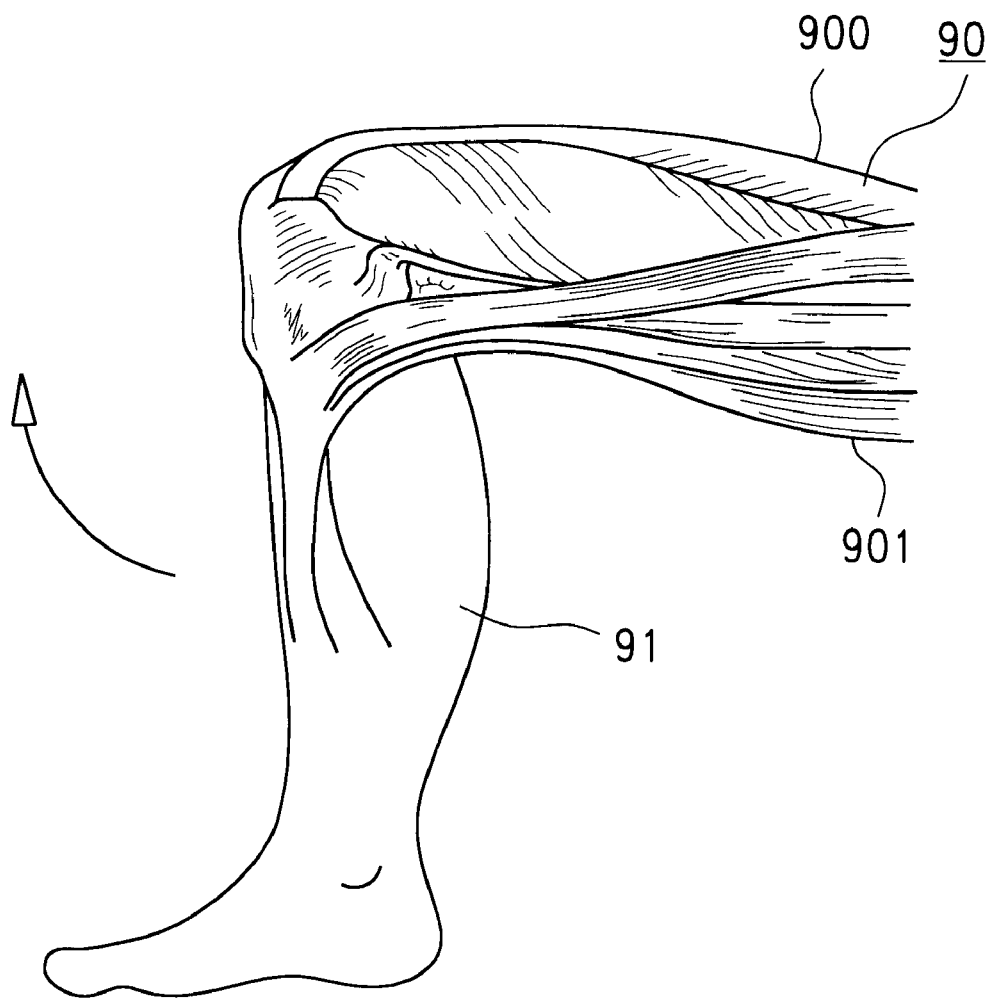
FIG. 3 is a pictorial illustration of various leg muscles involved with the knee in approximately 90 degrees of flexion.

FIG. 2 is a pictorial illustration of the muscle strengthening apparatus K embodying the invention which is applied to the upper and lower leg portions of the user or patient prior to flexing of the knee. FIG. 3 is a view similar to FIG. 2 showing various muscles involved in flexing of the knee.

During the practice of the present invention, the two electrodes 40, 41 may be applied to the upper and lower leg portions, respectively, of the user or patient, as illustrated in FIG. 2. Also, rotation of the knob 420 sets the change-over switch of the controller 42 to initiate electrode energization in response to the detection output of the sensor 31 in the manner as indicated at (1) above.

It should be noted that the extending action of the knee of the user or patient seated in a chair occurs as a result of contraction of the quadriceps muscle functioning as the agonist muscle. When the quadriceps muscle becomes contracted, the hamstring muscle functioning as the antagonist muscle is allowed to extend. It is to be noted that FIGS. 2 and 3 show the situation where no contraction or extension of the quadriceps and hamstring muscles takes place as the knee remains flexed.

Figure 4:
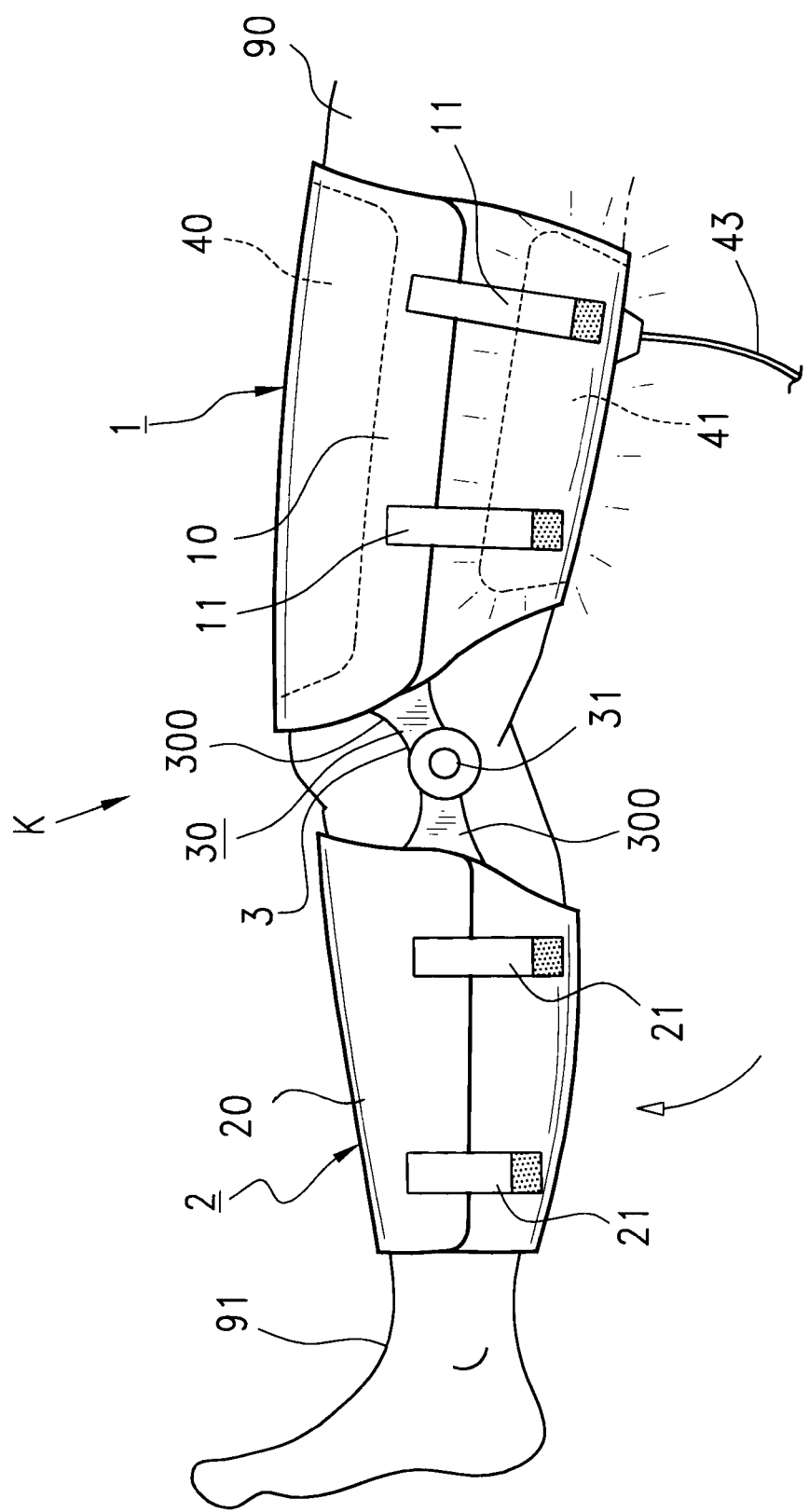
FIG. 4 is view similar to FIG. 2 but showing the leg in a fully extended position.
Figure 5:
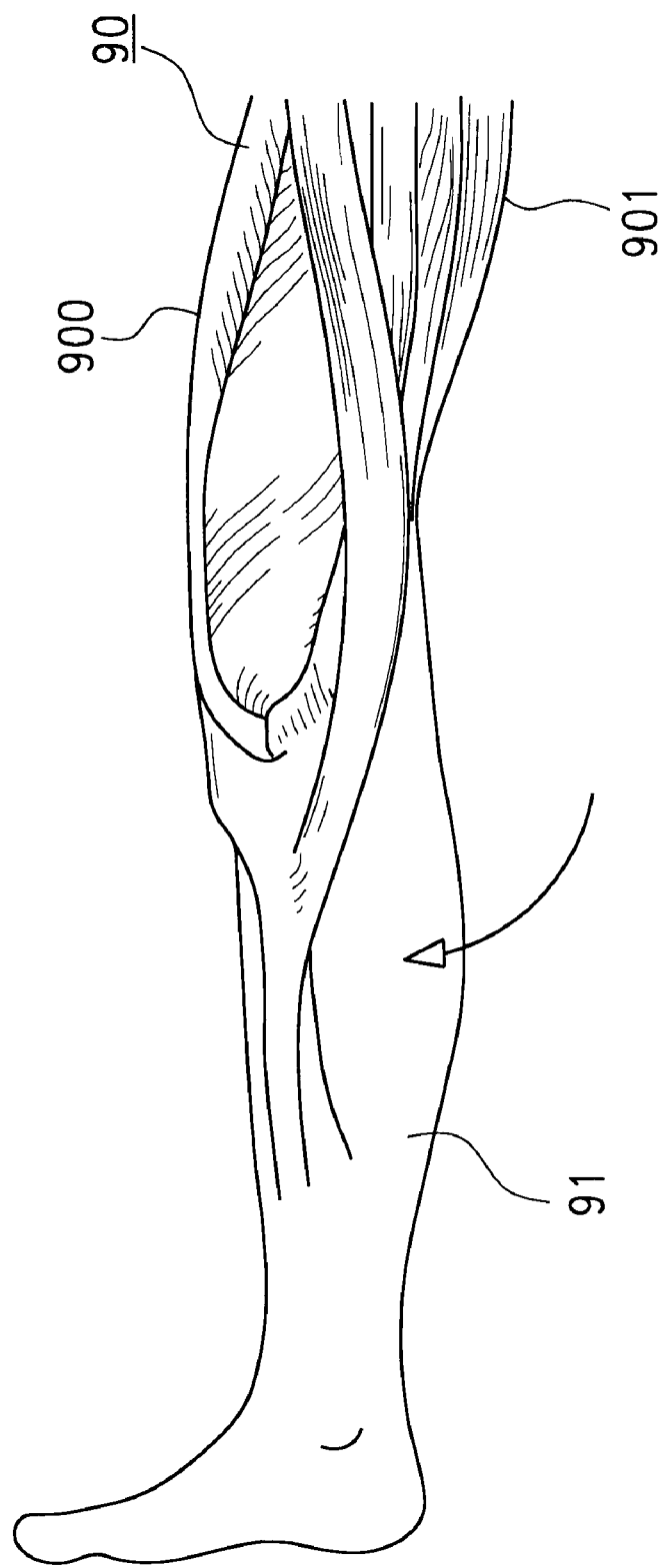
FIG. 5 is a pictorial illustration of the various leg muscles involved when the knee joint is fully extended.

Referring to FIGS. 4 and 5, as the next step, the patient or user attempts to actively extend the knee to raise the lower leg portion to a generally horizontal level. In so doing, the patient or user actively or volitionally contracts the quadriceps muscle functioning as the agonist muscle while, at the same time, allowing the hamstring muscle functioning as the antagonist muscle to extend. This motion of the leg is sensed by the sensor 31. Specifically, the sensor 31 provides a signal indicative of extending action of the knee and accordingly contraction of the quadriceps muscle to the controller 42 when the angle between the upper and lower leg portions exceeds a predetermined threshold value.

Detection of the extending action of the leg by the sensor 31 will trigger the controller 42 to provide an electrical signal of muscle stimulating amplitude and waveform to the electrodes 41 and thence to the hamstring muscle through the electrically conducting adhesive layer provided over the electrodes. In this manner, electrical stimulation is provided to the hamstring muscle, causing it to attempt to commence contraction. This will effectively produce the resistance to extending movement of the hamstring muscle. However, the knee overcomes the resistance and continues extending toward its full extent so that the hamstring muscle eventually becomes extended. It will be apparent from the foregoing description that the "eccentric contraction" occurs in the hamstring muscle and also that the "closed-kinetic-chain exercise" is applied for the knee joint because of co-contraction of the hamstring and quadriceps muscles.

Figure 6:
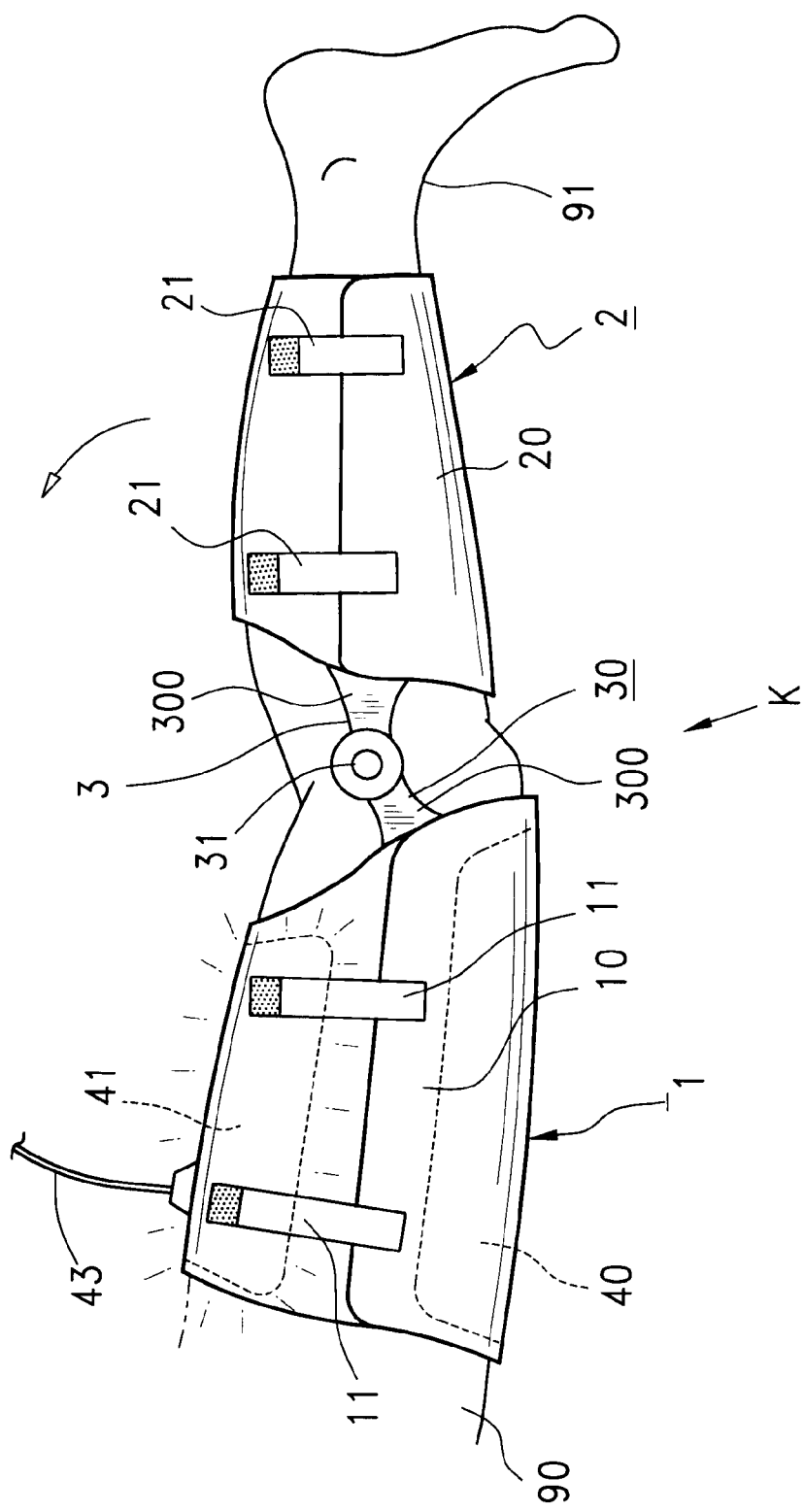
FIG. 6 is a view similar to FIG. 2 but showing the fully extended leg of a user lying with his or her face down.
Figure 7:
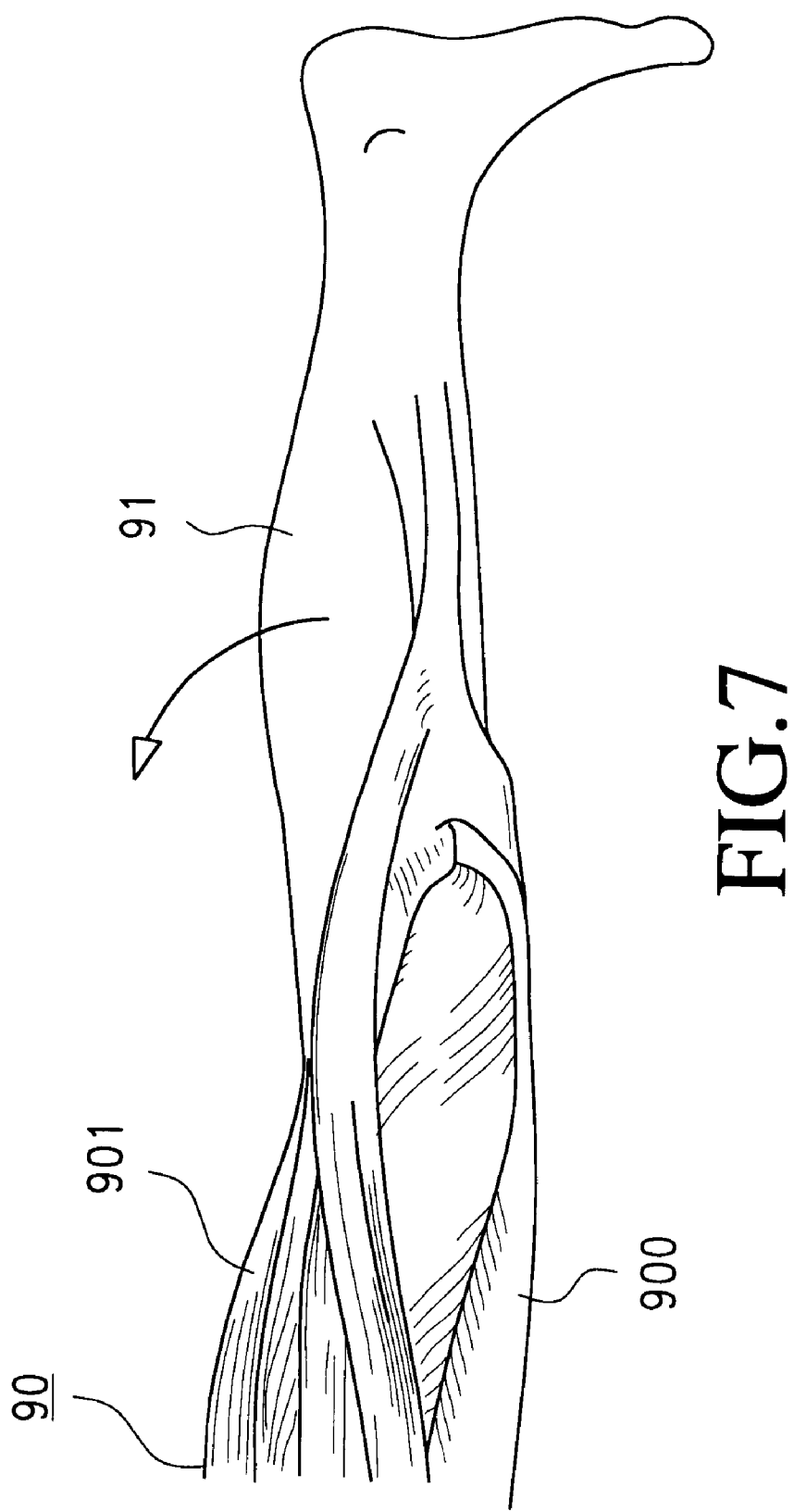
FIG. 7 is a view similar to FIG. 6 showing various leg muscles involved when the knee joint is fully extended.

Referring to FIGS. 6 and 7, only one leg of the user lying with his or her face down is shown as fully extended, with the muscle strengthening apparatus of the invention attached to the upper leg portion 90 and the lower leg portion 91. Although not specifically shown, the knob 420 is manually operated to set the controller 42 to cause electrode energization in response to the detection output of the sensor 31 in the manner as indicated at (3) above.

It should be noted that flexing of the knee of the user lying with his or her face down occurs as a result of contraction of the hamstring muscle which functions as the agonist muscle. When the hamstring muscle becomes contracted, the quadriceps muscle functioning as the antagonist muscle is allowed to extend. It is to be noted that FIGS. 6 and 7 show the situation where no contraction or extension of the hamstring and quadriceps muscles takes place as the knee remains extended.

Figure 8:
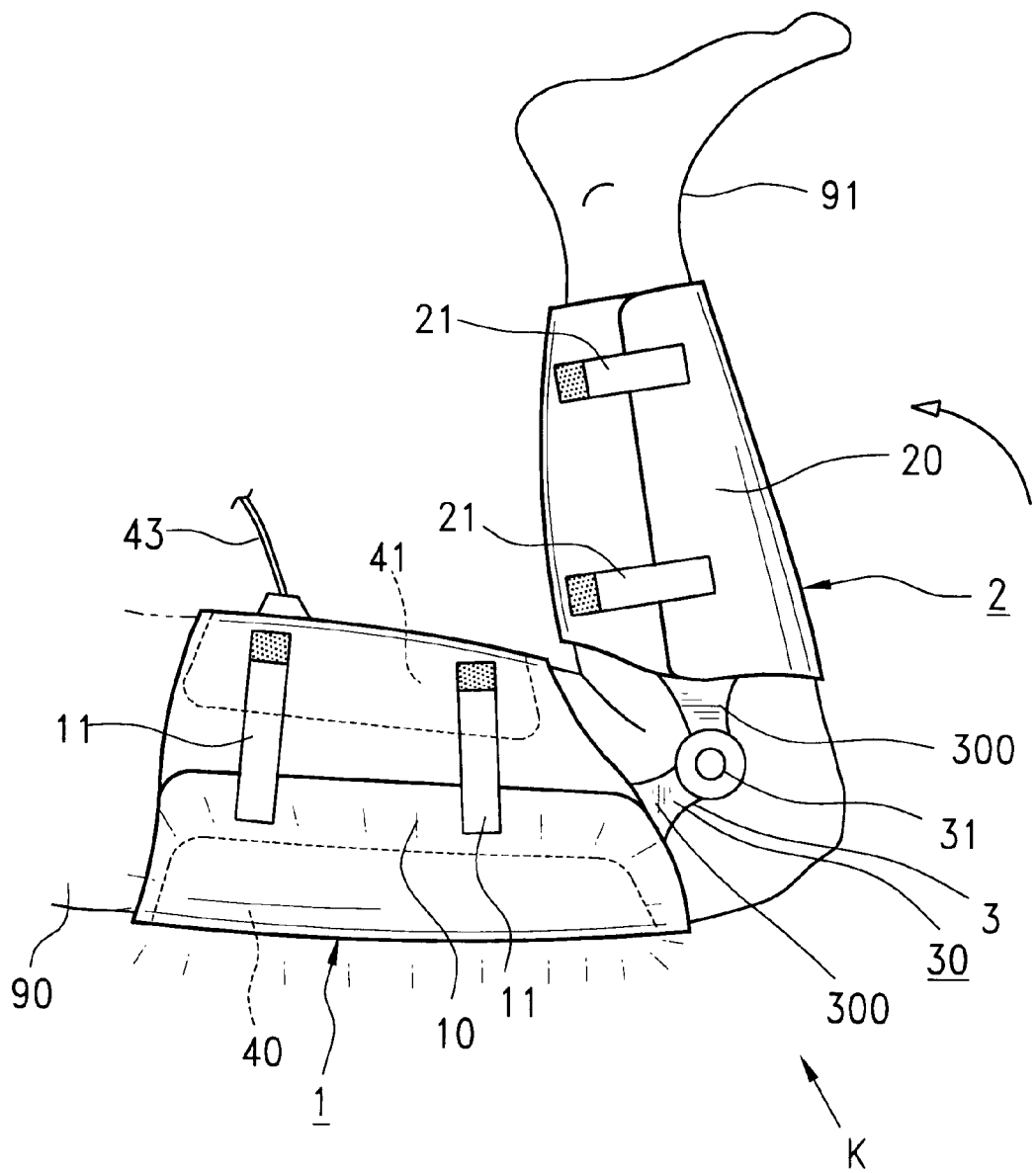
FIG. 8 is a view similar to FIG. 6 but showing the leg in a flexed position.
Figure 9:
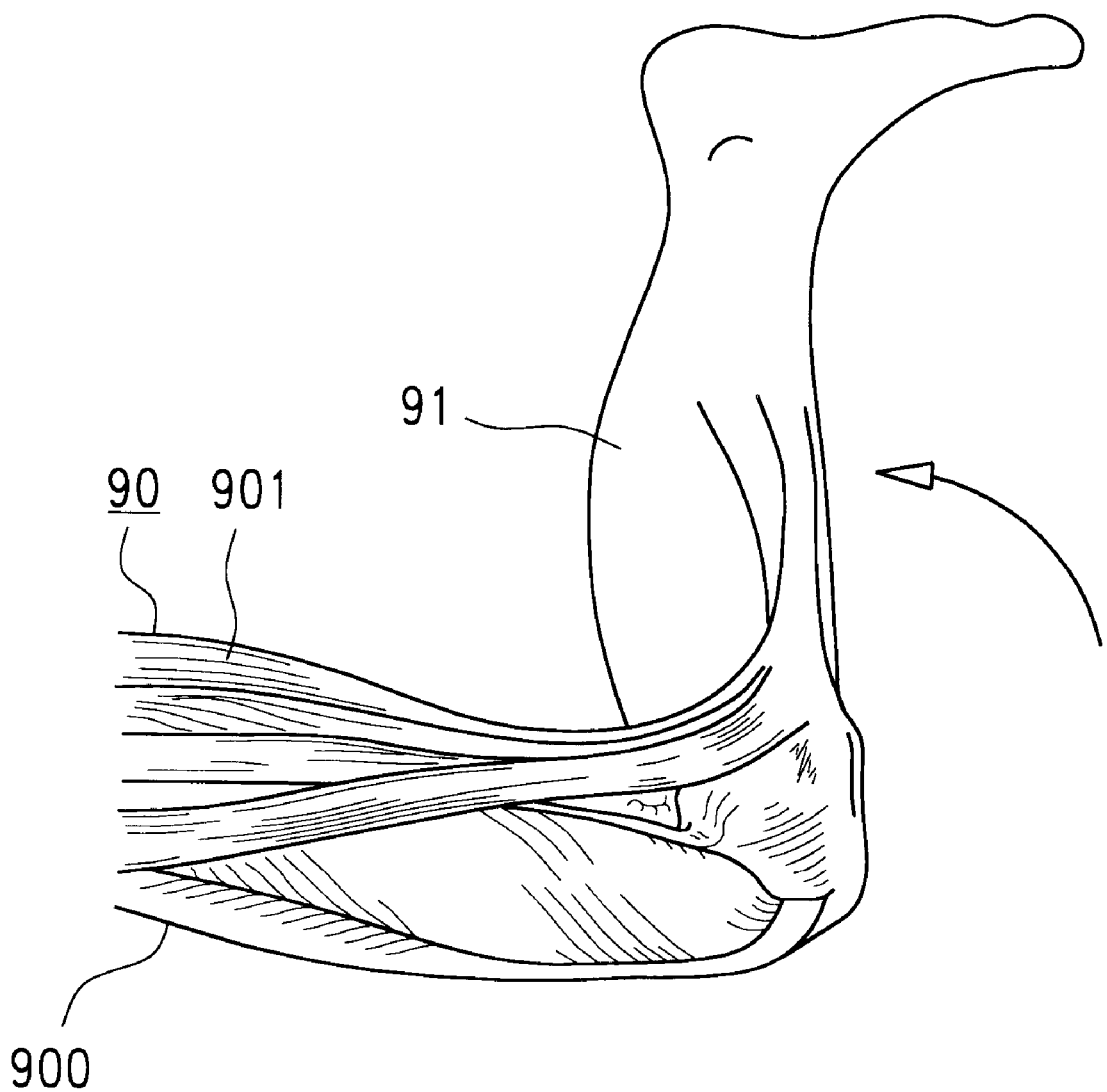
FIG. 9 is a pictorial illustration of the various leg muscles involved with the knee in approximately 90 degrees of flexion.

Referring to FIGS. 8 and 9, as the next step, the patient or user lying with his or her face down attempts to flex the knee actively or volitionally so as to move the foot portion 91 upwardly. In so doing, the patient or user actively or volitionally contracts the hamstring muscle functioning as the agonist muscle while, at the same time, allowing the quadriceps muscle functioning as the antagonist muscle to extend. This motion of the leg is sensed by the sensor 31 which provides a signal indicative of flexing of the knee and accordingly contraction of the hamstring muscle to the controller 42 when the angle between the upper and lower leg portions reaches a predetermined threshold value.

Detection of knee flexion by the sensor 31 will trigger the controller 42 to provide an electrical signal of muscle stimulating amplitude and waveform to the electrodes 40 and thence to the quadriceps muscle of the leg through the electrically conducting adhesive layer. Electrical stimulation is thus provided to the quadriceps muscle, causing it to attempt to begin contraction. This will result in the resistance to extending action of the quadriceps muscle. However, by overcoming the resistance, the knee continues flexing to move the lower leg portion to an upright position shown in FIG. 8 so that the quadriceps muscle eventually becomes extended. As will be apparent from the foregoing description, the quadriceps muscle experiences the "eccentric contraction" and also the "closed-kinetic-chain exercise" is applied for the knee joint because the contraction of the quadriceps muscle occurs simultaneously with the contraction of the hamstring muscle.

With the leg receiving the closed-kinetic-chain exercise accompanied by the eccentric contraction through electrical stimulation, the bone surrounded by the muscles involved is subjected to a compressive loading axially of the bone. It has been found that this axial compressive loading, if applied to bones in an appropriate manner, can effectively prevent osteoporosis which may be caused by the prolonged disuse of the limbs.

As described above, the lower portion 2 of the present apparatus is placed over the lower leg portion, and rotation thereof relative to the upper portion 1 is sensed by the goniometer 30. However, it should be noted that a combination of the lower portion 2, the goniometer 30 and the sensor 31 may be replaced with any other suitable means for detecting motion of the muscles involved, e.g., a myoelectric type sensor.

As described above, the muscle strengthening apparatus of the invention can provide electrical stimulation to an antagonist muscle when the sensor 31 detects motion of the agonist muscle through rotation of the goniometer 30, if the knob 420 is set to cause electrode energization as indicated at (1) or (3) above. Accordingly, if no motion of the knee joint and according its associated muscles is detected, the antagonist muscle will not receive any electrical stimulation from the controller 42.

It should be noted, however, that the present invention is not limited to the particular timing at which electrical stimulation is provided to an antagonist muscle as described above. For example, providing electrical stimulation to the antagonist muscle followed by active or volitional contraction of the agonist muscle should fall within the scope of the invention. The essence of the invention, as demonstrated by the claims, lies in that electrical stimulation is provided to the antagonist muscle when it is being extended and also when the agonist muscle is in a contracting state.

If the knob 420 for the change-over switch is set at position (2) or (4), it is possible to provide electrical stimulation to agonist muscles. It should be noted that the resulting contraction of the agonist muscles will assist the aged or paralyzed patients in performing certain actions.

With the knob 420 set at position (5) or (6), it is possible to provide electrical stimulation to the agonist muscles at any controlled timing in order to strengthen those muscles.

To capitulate the important features and the resultant advantages of the present invention:

(a) The present invention provides electrical stimulation to an antagonist muscle rather than an agonist muscle, when the agonist muscle is in a contracting state. This will cause "eccentric contraction" of the antagonist muscle, enabling exercizing in the so-called "closed-kinetic-chain" manner.

(b) The present invention does not rely on a mechanical loading of muscles thus provides a portable home gymnasium because it is relatively small, light-weight, easy to transport and also relatively simple in construction. The muscle strengthening apparatus of the invention is particularly suited for use by athletes who desire to hand-carry such apparatus during playing tours and also for astronauts who need exercising muscles during their extended stay in the outer space in order to prevent deterioration of muscles due to disuse.

(c) The present invention permits a user or patient to exercise in a comfortable posture for an extended period of time thus providing a muscle strengthening apparatus particularly suitable for rehabilitation of severely injured patients.

(d) The present invention can effectively prevent osteoporosis which may be caused by the prolonged disuse of the limbs, because the bones surrounded by muscles involved in the closed-kinetic-chain exercise are subjected to a compressive loading axially of the bones.

(e) The muscle strengthening apparatus of the invention can easily be modified to provide electrical stimulation to agonist muscles to cause forced contraction thereof. This will assist severely injured patients in actively functioning their paralyzed muscles. While the description above relates to particular embodiments of the present invention, it will be understood that many modifications may be made without departing from the spirit thereof. The presently disclosed embodiments are therefore to be considered in all aspects as illustrative and not restrictive, the scope of the invention being indicated by the appended claims, rather than the foregoing description, and all changes which come within the meaning and range of equivalency of the claims are therefore intended to be embraced therein.

What is claimed is:

1. Apparatus for strengthening muscles, comprising:

first means for providing electrical stimulation to an antagonist muscle;

second means for sensing a volitionally generated contraction of an agonist muscle; and third means responsive to said second means for actuating said first means to cause eccentric contraction of said antagonist muscle thereby providing resistance to said volitionally generated against muscle contraction.

2. Apparatus as set forth in claim 1 wherein said second means provides a contraction signal indicative of contraction of said agonist muscle, said third means being operative to actuate said first means in response to said contraction signal.

3. Apparatus as set forth in claim 2 wherein said third means comprises fourth means for receiving said contraction signal from said second means and for transmitting an electric signal of muscle stimulating amplitude and waveform to said first means, said first means comprises fifth means for receiving said electric signal of muscle stimulating amplitude and waveform from said fourth means and for transmitting said electric signal to said antagonist muscle to cause eccentric contraction thereof.

4. Apparatus as set forth in claim 3 wherein said second means comprises:
   an upper portion adapted to be placed on an upper leg portion of a leg;
   a lower portion adapted to be placed on a lower leg portion of the leg; and
   an interconnecting portion adapted to join said upper and lower portions for pivotal movement with respect to each other.

5. Apparatus as set forth in claim 4 wherein said second means further comprises:
   a goniometer operatively associated with said interconnecting portion to measure the angle at which said upper portion and lower portion make; and
   a sensor operatively associated with said goniometer to provide said contraction signal to said third means when the angle measured by said goniometer exceeds a predetermined threshold value.

6. Apparatus as set forth in claim 5 wherein said second means provides said contraction signal when a user in a sitting posture actively extends his knee, said fourth means being responsive to said contraction signal for transmitting said electric signal to said first means so that electrical stimulation may be provided to a hamstring muscle functioning as said antagonist muscle to cause eccentric contraction thereof.

7. Apparatus as set forth in claim 5 wherein said second means provides said contraction signal when a user lying on his face down actively flexes his knee, said fourth means being responsive to said contraction signal for transmitting said electric signal to said first means so that electrical stimulation may be provided to a quadriceps muscle functioning as said antagonist muscle to cause eccentric contraction thereof.

8. Apparatus as set forth in claim 1 further comprising:
   sixth means for providing electrical stimulation to said agonist muscle; and
   seventh means responsive to said second means for actuating said sixth means to induce contraction of said agonist muscle.

9. Apparatus as set forth in claim 8 wherein said second means provides said contraction signal when a user in a sitting posture actively extends his knee, said seventh means being responsive to said contraction signal for transmitting an electric signal of muscle stimulating amplitude and waveform to said sixth means so that electrical stimulation may be provided to a quadriceps muscle functioning as said agonist muscle to induce contraction thereof.

10. Apparatus as set forth in claim 8 wherein said second means provides said contraction signal when a user lying on his face down actively flexes his knee, said seventh means being responsive to said contraction signal for transmitting an electric signal of muscle stimulating amplitude and waveform to said sixth means so that electrical stimulation may be provided to a hamstring muscle functioning as said agonist muscle to induce contraction thereof.

11. Apparatus as set forth in claim 8 further comprising eighth means for selectively actuating said first and sixth means to induce contraction of said antagonist and agonist muscles irrespective of the operation of said second means.

12. Apparatus for strengthening muscles comprising:
   means for generating an electrical signal of muscle stimulating amplitude and waveform;
   surface electrode means in electrical communication with said signal generation means for applying said electric signal to an antagonist muscle;
   sensor means for sensing a volitionally generated contraction of an agonist muscle and providing a contraction signal indicative of such contraction of said agonist muscle; and
   controller means in electrical communication with said signal generation means and said sensor means for controlling the operation of said signal generation means to cause eccentric contraction of said antagonist muscle in response to said contraction signal to thereby provide resistance to said volitionally generated against muscle contraction.

13. Apparatus as set forth in claim 12 further comprising:
   second surface electrode means in electrical communication with said signal generation means for applying said electric signal to said agonist muscle, said controller means being operative to control the operation of said signal generation means to cause contraction of said agonist muscle.

* * * * *

UNITED STATES PATENT AND TRADEMARK OFFICE
CERTIFICATE OF CORRECTION

PATENT NO. : 6,456,885 B1 Page 1 of 1
APPLICATION NO. : 09/536695
DATED : September 24, 2002
INVENTOR(S) : Shiba et al.

It is certified that error appears in the above-identified patent and that said Letters Patent is hereby corrected as shown below:

Claim 1, column 8, line 65, please delete "against" and insert therein -- agonist --.

Claim 12, column 10, line 40, please delete "against" and insert therein -- agonist --.

Signed and Sealed this

Twenty-second Day of May, 2007

JON W. DUDAS
*Director of the United States Patent and Trademark Office*